(12) United States Patent
Guo et al.

(10) Patent No.: US 11,684,271 B2
(45) Date of Patent: Jun. 27, 2023

(54) WEARABLE DEVICE FOR SENSING VITAL SIGNS

(71) Applicant: Welch Allyn, Inc., Skaneateles Falls, NY (US)

(72) Inventors: Lei Guo, Camillus, NY (US); Thaddeus J. Wawro, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 136 days.

(21) Appl. No.: 17/182,355

(22) Filed: Feb. 23, 2021

(65) Prior Publication Data

US 2021/0275038 A1 Sep. 9, 2021

Related U.S. Application Data

(60) Provisional application No. 62/985,389, filed on Mar. 5, 2020.

(51) Int. Cl.
*A61B 5/0205* (2006.01)
*A61B 5/021* (2006.01)
(Continued)

(52) U.S. Cl.
CPC ........ *A61B 5/0205* (2013.01); *A61B 5/02141* (2013.01); *A61B 5/14552* (2013.01);
(Continued)

(58) Field of Classification Search
CPC .............. A61B 5/0205; A61B 5/02141; A61B 5/14552; A61B 5/7282; A61B 7/04;
(Continued)

(56) References Cited

U.S. PATENT DOCUMENTS 8,442,607 B2 5/2013 Banet et al.
8,506,480 B2 8/2013 Banet et al.
(Continued)

FOREIGN PATENT DOCUMENTS

EP 2742853 A1 6/2014
EP 2932729 B1 9/2016
(Continued)

OTHER PUBLICATIONS

Gau, M., et al., "Comparison of noninvasive pulse transit time estimates as markers of blood pressure using invasive pulse transit time measurements as a reference," Physiological Reports, May 2016; 4(10): e12768, 11 pages.
(Continued)

*Primary Examiner* — Eric F Winakur
*Assistant Examiner* — Abid A Mustansir
(74) *Attorney, Agent, or Firm* — Merchant & Gould P.C.

(57) ABSTRACT

A wearable device for sensing vital signs includes a housing defining an interior cavity. An optical unit is positioned inside the interior cavity. The optical unit includes one or more light emitters that emit optical signals, at least one polarizer orientated to block optical signals having a predetermined polarity direction, and one or more light sensors that receive optical signals that pass through the at least one polarizer. An acoustic unit is positioned inside the interior cavity, and has a microphone to receive acoustic signals that enter into the interior cavity. The acoustic signals are used to non-invasively estimate blood pressure.

15 Claims, 7 Drawing Sheets

(51) Int. Cl.
*A61B 5/1455* (2006.01)
*A61B 5/00* (2006.01)
*A61B 7/04* (2006.01)
*A61B 5/145* (2006.01)

(52) U.S. Cl.
CPC .............. *A61B 5/7282* (2013.01); *A61B 7/04* (2013.01); *A61B 5/0022* (2013.01); *A61B 5/02125* (2013.01); *A61B 5/14546* (2013.01); *A61B 5/7207* (2013.01); *A61B 5/746* (2013.01); *A61B 2562/0242* (2013.01)

(58) Field of Classification Search
CPC .............. A61B 5/0022; A61B 5/02125; A61B 5/14546; A61B 5/7207; A61B 5/746; A61B 2562/0242; A61B 2562/0204; A61B 5/021; A61B 5/02427; A61B 5/14551; A61B 5/6823; A61B 5/0095
See application file for complete search history.

(56) References Cited

U.S. PATENT DOCUMENTS

| | | | |
|---|---|---|---|
| 2005/0119711 A1* | 6/2005 | Cho ..................... | A61B 5/4818 607/42 |
| 2008/0082004 A1 | 4/2008 | Banet et al. | |
| 2013/0109949 A1* | 5/2013 | Li ..................... | G01N 21/4738 600/407 |
| 2013/0190589 A1* | 7/2013 | Chen ..................... | A61B 5/145 600/407 |
| 2015/0005613 A1* | 1/2015 | Kim ................... | G01N 29/2418 600/407 |
| 2017/0209052 A1 | 7/2017 | Nakamura | |
| 2018/0206747 A1 | 7/2018 | Rinderknecht et al. | |
| 2018/0325397 A1* | 11/2018 | Presura .............. | A61B 5/02255 |
| 2019/0133516 A1 | 5/2019 | Banet et al. | |
| 2019/0150739 A1 | 5/2019 | Wawro et al. | |

FOREIGN PATENT DOCUMENTS

| | | |
|---|---|---|
| EP | 3223540 A1 | 9/2017 |
| WO | 2013151099 A1 | 10/2013 |
| WO | 2020023681 A1 | 1/2020 |

OTHER PUBLICATIONS

Wang, R., et al., "Cuff-Free Blood Pressure Estimation Using Pulse Transit Time and Heart Rate," Int. Conf. Signal Process Proc., Author manuscript, Oct. 2014; 2014:115-118, 10 pages.

Dastjerdi, A.E., et al., "Non-invasive blood pressure estimation using phonocardiogram," IEE Xplore Digial Library, IEE Conference Publication, IEEE International Symposium, 2017, 2 pages.

European Search Report, EP 21 16 0324, dated Aug. 19, 2021, 8 pages.

* cited by examiner

WEARABLE DEVICE FOR SENSING VITAL SIGNS

BACKGROUND

Vital sign measurements are taken to help assess the general physical health of a subject, give clues to possible diseases, and show progress toward recovery. One type of vital sign that is often measured is blood oxygen saturation which is the fraction of oxygen-saturated hemoglobin relative to total hemoglobin in the blood of the subject. Normal blood oxygen saturation levels in humans are 95-100 percent. Blood oxygen saturation levels below 90 percent are considered deficient and are diagnosed as hypoxemia. Blood oxygen saturation levels below 80 percent may compromise organ function, such as the brain and heart, and should be promptly addressed. Continued low oxygen levels may lead to respiratory or cardiac arrest.

Another vital sign that is often measured is blood pressure which is the pressure of circulating blood on the walls of blood vessels. Blood pressure results from the heart pumping blood through the circulatory system and is usually expressed in terms of the systolic pressure (maximum pressure during one heartbeat) over diastolic pressure (minimum pressure in between two heartbeats). Blood pressure is typically measured using an inflatable cuff to collapse and then release the artery under the cuff in a controlled manner to measure the pressure.

SUMMARY

In general terms, the present disclosure relates to a wearable device for sensing vital signs. In one possible configuration, the wearable device provides a technical effect by sensing the blood oxygen saturation level of a subject when attached to a portion of the subject's body that has low blood perfusion and that is ordinarily unable to provide useful data for measuring blood oxygen saturation. In yet another possible configuration, the wearable device provides a technical effect by measuring both the blood oxygen saturation and blood pressure of the subject simultaneously when attached to a portion of the subject's body. Various aspects are described in this disclosure, which include, but are not limited to, the following aspects.

In one aspect, a wearable device for sensing vital signs comprises: a housing defining an interior cavity; an optical unit positioned inside the interior cavity, the optical unit having: one or more light emitters that emit optical signals; at least one polarizer orientated to block optical signals having a predetermined polarity direction; and one or more light sensors that receive optical signals that pass through the at least one polarizer; and an acoustic unit positioned inside the interior cavity, the acoustic unit having: a microphone to receive acoustic signals that enter into the interior cavity, the acoustic signals being used to non-invasively estimate blood pressure.

In another aspect, a wearable device for sensing vital signs comprises: a housing defining an interior cavity; an optical unit positioned inside the interior cavity, the optical unit having: one or more light emitters that emit optical signals; a first polarizer orientated to polarize the optical signals emitted from the one or more light emitters in a first polarity direction; a second polarizer orientated with respect to the second polarizer to block optical signals reflected in the first polarity direction; and one or more light sensors that receive reflected optical signals that pass through the second polarizer, the reflected optical signals being used to non-invasively measure peripheral oxygen saturation.

In another aspect, a method for obtaining vital signs comprises: emitting polarized optical signals; filtering optical signals that do not penetrate into a tissue; receiving the filtered optical signals; and using the filtered optical signals to measure a vital sign.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
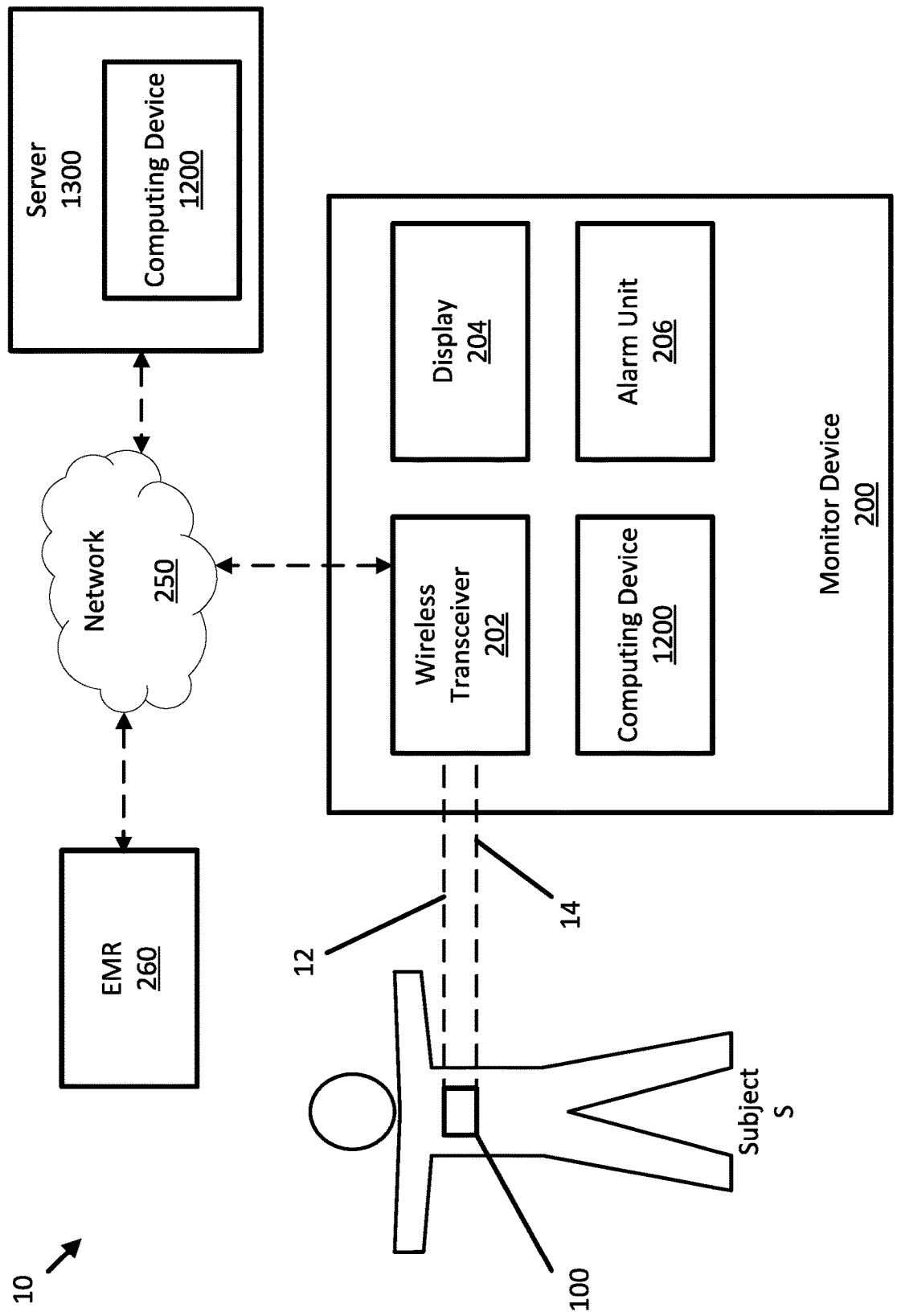
FIG. 1 schematically illustrates a patient monitoring system.

FIG. 1 is a schematic view of a patient monitoring system 10 that includes a wearable device 100 that can be worn by a subject S to measure one or more vital signs. The wearable device 100 is "wearable" in that it can be applied to a subject's skin and will resist unintentional dislodgement over a specified interval of time In one embodiment, the wearable device 100 is used to measure peripheral oxygen saturation ($SpO_2$) of the subject S by calculating a difference in absorption between oxygenated and deoxygenated hemoglobin in the blood of the subject S. In this embodiment, the wearable device 100 can be attached to any area of the body of the subject S including the chest to detect a first set of signals 12 for sensing $SpO_2$. The wearable device 100 amplifies and removes noise from the first set of signals 12 to improve the quality of the $SpO_2$ measurements.

In another embodiment, the wearable device 100 is used to measure both the $SpO_2$ and blood pressure of the subject S by detecting the first set of signals 12 for sensing $SpO_2$ and detecting a second set of signals 14 for sensing blood pressure. Advantageously, the wearable device 100 can be used to non-invasively measure blood pressure without using an inflatable cuff. Instead, the wearable device 100 is attached to the chest of the subject S. The wearable device 100 simultaneously detects the first and second sets of signals 12, 14 such that the blood pressure and $SpO_2$ of the subject S can be simultaneously measured. In this embodiment, the wearable device 100 both amplifies the first and second sets of signals 12, 14 and removes noise from these signals to improve the quality of the $SpO_2$ and blood pressure measurements.

As shown in FIG. 1, the wearable device 100 transmits the first and second sets of signals 12, 14 to a monitor device 200. In one embodiment, the monitor device 200 is a smartphone, tablet computer, or other portable computing device. In another embodiment, the display device is a vital signs monitor that can be fixed to a wall or to another device within a facility such as a bed, or is a portable spot monitor that can be moved about the facility.

The first and second sets of signals 12, 14 are wirelessly transmitted to a wireless transceiver 202 of the monitor device 200 such that the wearable device 100 is not tethered to the monitor device 200. Advantageously, the wireless transmission allows the subject S to move freely relative to the monitor device 200 and thereby enhances the mobility of the subject S while the wearable device 100 is worn by the subject S. Examples of the wireless transmission between the wearable device 100 and the monitor device 200 can include, without limitation, Bluetooth, Wi-Fi, RFID, Near-Field Communication (NFC), ZigBee, and the like.

In one embodiment, the first and second sets of signals 12, 14 are raw data that is processed by the monitor device 200 to determine the $SpO_2$ and blood pressure measurements. The monitor device 200 includes a computing device 1200 for processing the first and second sets of signals 12, 14. The computing device 1200 includes at least one processing unit and a memory (which are described in more detail below with reference to FIG. 7). The memory of the computing device 1200 stores one or more algorithms that are performed by the processing unit of the computing device 1200 to calculate the $SpO_2$ and blood pressure measurements.

In another embodiment, the patient monitoring system 10 includes a server 1300 that is remotely located with respect to the wearable device 100 and monitor device 200. In this embodiment, the monitor device 200 transmits the first and second sets of signals 12, 14 as raw data to the server 1300 via a network 250, and the server 1300 uses a computing device 1200 to process the first and second sets of signals 12, 14 to determine the $SpO_2$ and blood pressure measurements of the subject S. The calculated $SpO_2$ and blood pressure measurements are then communicated back to the monitor device 200 and/or wearable device 100 via the network 250.

The network 250 can include any type of wired or wireless connections or any combinations thereof. Examples of wireless connections include digital cellular network connections such as 5G. In some embodiments, wireless connections can be accomplished using Bluetooth, Wi-Fi, RFID, NFC, ZigBee, and the like.

In another embodiment, the wearable device 100 processes the raw data itself to determine the $SpO_2$ and blood pressure measurements such that the first and second sets of signals 12, 14 are calculated measurements. In this embodiment, the wearable device 100 include a computing device that includes at least one processing unit and a memory (e.g., such as those described below with reference to FIG. 7).

In further embodiments, the processing of the raw data to determine the $SpO_2$ and blood pressure measurements is shared between the wearable device 100, the monitor device 200, and/or the server 1300, and may vary depending on one or more system parameters including, but not limited to, the processing capacities of the respective devices, the battery levels of the respective devices, energy cost of transmitting the first and second sets of signals 12, 14, the levels of noise in the first and second sets of signals 12, 14, and/or the link rate and link reliability for linking the respective devices together, and the like.

The monitor device 200 includes a display 204 for displaying the determined $SpO_2$ and blood pressure measurements of the subject S. In some examples, the display 204 displays the determined $SpO_2$ and blood pressure measurements numerically, graphically, or in a combination of numerical and graphical representations. In some examples, the determined $SpO_2$ and blood pressure measurements are displayed on the wearable device 100 while worn by the subject S in addition or as an alternative to being displayed on the display 204.

The monitor device 200 further includes an alarm unit 206. The alarm unit 206 generates one or more alarms when the determined $SpO_2$ and blood pressure measurements are outside a predetermined limit. In some examples, the alarm unit 206 generates visual alarms on the display 204, audible alarms, and the like. In some further examples, in addition to or as an alternative to generating visual and/or audible alarms, the alarm unit 206 generates a message sent directly to one or more caregivers to notify the caregivers that the determined $SpO_2$ and blood pressure measurements are outside a predetermined limit. Examples of such messages can include text messages, instant messages, emails, and the like.

The monitor device 200 is in communication with the network 250 for transmitting the determined $SpO_2$ and blood pressure measurements to an electronic medical record system 260 (alternatively termed electronic health record, EMR/EHR). The determined $SpO_2$ and blood pressure measurements can be stored in an electronic medical record or electronic health record associated with the subject S.

Figure 2:
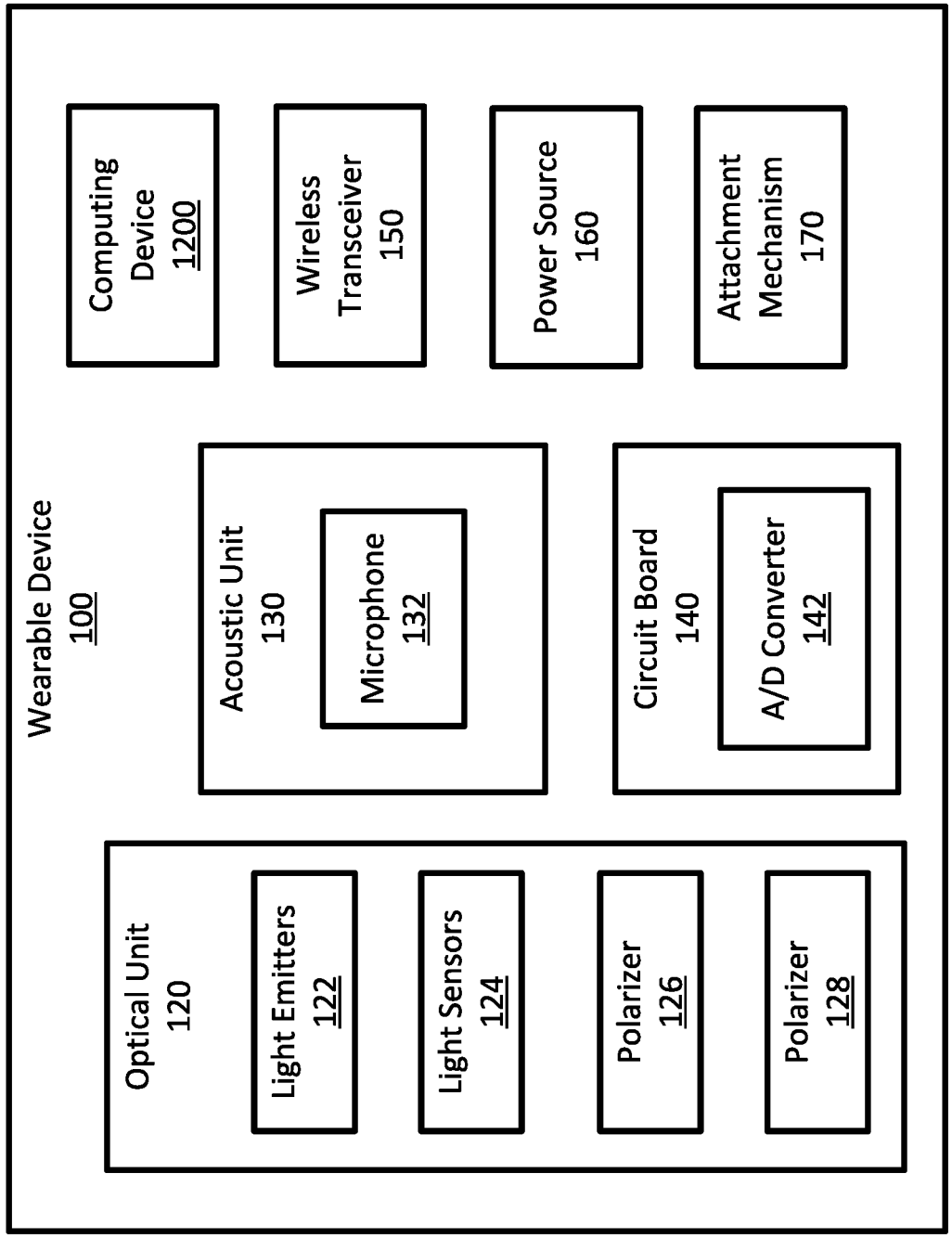
FIG. 2 schematically illustrates a wearable device for sensing vital signs.

FIG. 2 schematically illustrates the wearable device 100. As shown in FIG. 2, the wearable device 100 includes an optical unit 120 that detects the first set of signals 12 for sensing $SpO_2$ and an acoustic unit 130 that detects the second set of signals 14 for sensing blood pressure. In some examples, the optical unit 120 is a photoplethysmogram (PPG) sensor while the acoustic unit 130 is a phonocardiogram (PCG) sensor. Preferably, the wearable device 100 includes both the optical unit 120 and acoustic unit 130 in a single assembly to provide a small, lightweight, and easy to integrate sensor package for measuring both $SpO_2$ and blood pressure. In alternative examples the wearable device 100 may include only the optical unit 120.

The optical unit 120 includes one or more light emitters 122 to transmit optical signals to illuminate a portion of the body of the subject S, one or more light sensors 124 to receive optical signals reflected back from the illuminated portion of the body of the subject S, and first and second polarizers 126, 128 that are used to filter the reflected optical signals.

The light emitters 122 emit optical signals in the form of infrared (IR) and visible red light. The light emitters 122 can be LEDs, lasers, lamps, and the like.

In one embodiment, the light emitters 122 include a pair of LEDs with one LED emitting visible red light with a wavelength of about 660 nm, and the other LED emitting infrared light with a wavelength of about 940 nm. Absorption of light at these wavelengths differs significantly between blood loaded with oxygen and blood lacking oxygen. Oxygenated hemoglobin absorbs more infrared light and allows more visible red light to pass through. Deoxygenated hemoglobin allows more infrared light to pass through and absorbs more visible red light. The pair of LEDs can sequence the transmission of the red and infrared light to allow the light sensors 124 to respond to the red and infrared light separately.

The amount of absorption for each wavelength of light is measured. The ratio of the red light absorption to the infrared light absorption is calculated which represents the ratio of oxygenated hemoglobin to deoxygenated hemoglobin, and this ratio is converted to an $SpO_2$ measurement by using a lookup table. The amount of absorption for each wavelength of light can also be used to generate a plethysmograph and to evaluate blood perfusion.

The light sensors 124 measure changes in the infra-red (IR) and red light absorption in the blood of the subject S where the wearable device 100 is attached. In some examples, the light sensors 124 are photodetectors or photodiodes.

The first and second polarizers 126, 128 are optical filters that let light waves of a specific polarization to pass through while blocking light waves that are not polarized. The first polarizer 126 polarizes the optical signals emitted from the light emitters 122 into a beam of polarized light, and the second polarizer 128 filters the optical signals reflected back from the body to reduce noise in the reflected optical signals received by the light sensors 124. In embodiments where the light emitters 122 are lasers, the emitted light is already linearly polarized such that the first polarizer 126 is not needed in such a configuration.

In some embodiments, in addition to sensing $SpO_2$, the optical unit 120 is also used to measure photoplethysmogram (PPG) signals of the subject S that can be used to detect blood volume changes in the subject S. The PPG signals are obtained by using the optical unit 120 to illuminate a microvascular bed of tissue and measure changes in light absorption.

The acoustic unit 130 includes a microphone 132 to record acoustic signals from the heart of the subject S during a cardiac cycle. In embodiments where the wearable device 100 includes the acoustic unit 130, the wearable device 100 is preferably attached to the chest of the subject S. In some examples, the wearable device 100 is attached to a position of the chest adjacent to the sternum and in the second intercostal space between the ribs below the clavicle such that the microphone 132 is positioned next to the heart. The acoustic signals, also referred to herein as PCG signals, detect heart sounds that result from vibrations caused by the closing of heart valves and are used for non-invasive blood pressure (NIBP) algorithms.

In some embodiments, the optical and acoustical signals obtained by the optical unit 120 and acoustic unit 130, respectively, can be used to calculate a pulse transit time (PTT) which is the time it takes a pulse pressure waveform to propagate through a length of an artery. The PTT is the time delay of blood flow waveforms which closely correlates to blood pressure, and can be used to estimate both systolic and diastolic blood pressure. The PTT can be calculated from the detected blood volume changes which are determined from the optical signals obtained by the optical unit 120 and from the heart sounds obtained by the acoustic unit 130.

Still referring to FIG. 2, the wearable device 100 includes a circuit board 140 to mechanically support and electrically connect the various electronic components of the wearable device 100. The circuit board 140 can include an analog to digital converter 142.

The wearable device 100 further includes a computing device 1200 for processing the optical and acoustical signals from the optical unit 120 and acoustic unit 130, respectively. The computing device 1200 includes at least one processing unit and a memory. In some embodiments, the memory stores algorithms that when performed by the processing unit calculate the $SpO_2$ and blood pressure of the subject S. Once calculated, a wireless transceiver 150 can transmit the $SpO_2$ and blood pressure values to the monitor device 200 for display on the display 204. Alternatively, the wireless transceiver 150 can transmit raw data (i.e., the optical and acoustical signals from the optical and acoustic units 120, 130) to the monitor device 200, and the monitor device 200 performs the algorithms to calculate the $SpO_2$ and blood pressure of the subject S, or the monitor device 200 forwards the raw data to the server 1300 and the server 1300 performs the algorithms to calculate the $SpO_2$ and blood pressure of the subject S.

With respect to $SpO_2$, an algorithm stored in a memory of either the wearable device 100, monitor device 200, or server 1300 is used to calculate the $SpO_2$ of the subject S. As an example, an algorithm to calculate the $SpO_2$ of the subject S can be expressed as follows:

$$SpO_2 = \frac{HbO_2}{HbO_2 + Hb}$$

where $HbO_2$ is oxygenated hemoglobin and Hb is deoxygenated hemoglobin. The oxygenated and deoxygenated hemoglobin are detected by the optical unit 120 from the optical signals that are reflected back from the body and received by the light sensors 124.

With respect to blood pressure, one or more algorithms stored in a memory of either the wearable device 100 or monitor device 200 are used to calculate the pulse transit time (PTT) from the PPG and PCG signals. For example, the PTT can be calculated as the time delay between the PCG and PPG waveforms. Alternatively, the PTT can be calculated as the time delay between proximal and distal PPG waveforms. Thereafter, the calculated PTT is used to estimate the systolic blood pressure and diastolic blood pressure of the subject S.

The wearable device 100 further includes a power source 160 to power the various components of the wearable device 100 including the components of the optical unit 120 such as the light emitters 122 and light sensors 124 and the components of the acoustic unit 130 including the microphone 132. As an example, the power source 160 can include disposable or rechargeable batteries. Alternative power sources are possible.

The wearable device 100 can include an attachment mechanism 170 to secure the wearable device 100 to the body of the subject S. A variety of attachment mechanisms 170 can be used. For example, an adhesive can be used to secure the wearable device 100 to the body of the subject S. Alternatively, the wearable device 100 can be incorporated into a strap or clothing that can be tightly fitted around the body of the subject S such that the wearable device 100 is snuggly attached up against a body surface such as the chest wall of the subject S.

The wearable device 100 can be included in an assembly that includes additional components and sensors. For example, the wearable device 100 can be included in a patch worn by the subject S that includes additional sensors such as ECG electrodes, temperature sensors, and the like. In some embodiments, the wearable device 100 is included in a patch that can noninvasively determine various vital signs such as body temperature, blood pressure, pulse (i.e., heart rate), and breathing rate. In some further embodiments, the wearable device 100 is included in a patch that calculate an early warning score based on the noninvasively determined vitals.

Figure 3:
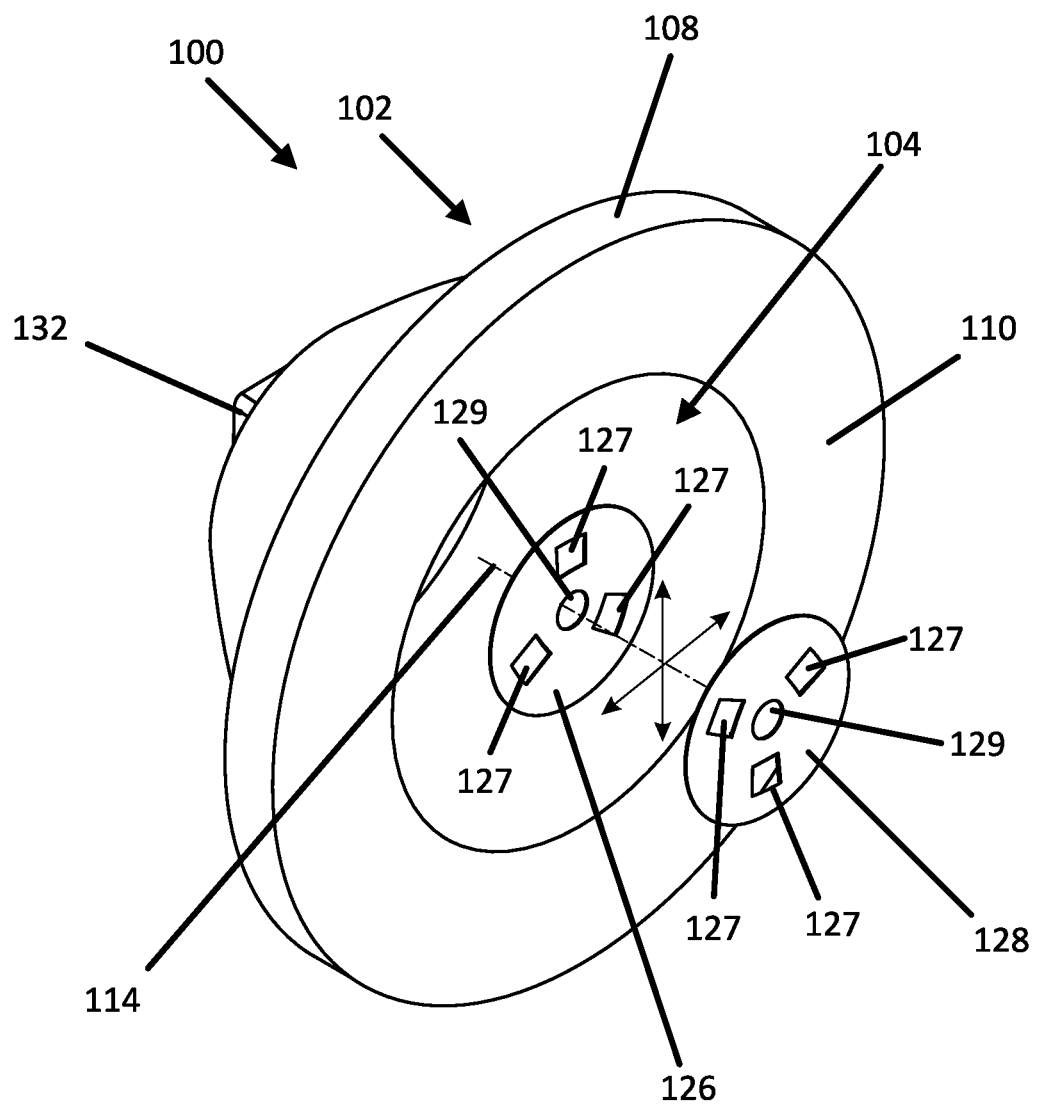
FIG. 3 illustrates a housing of the wearable device.
Figure 4:
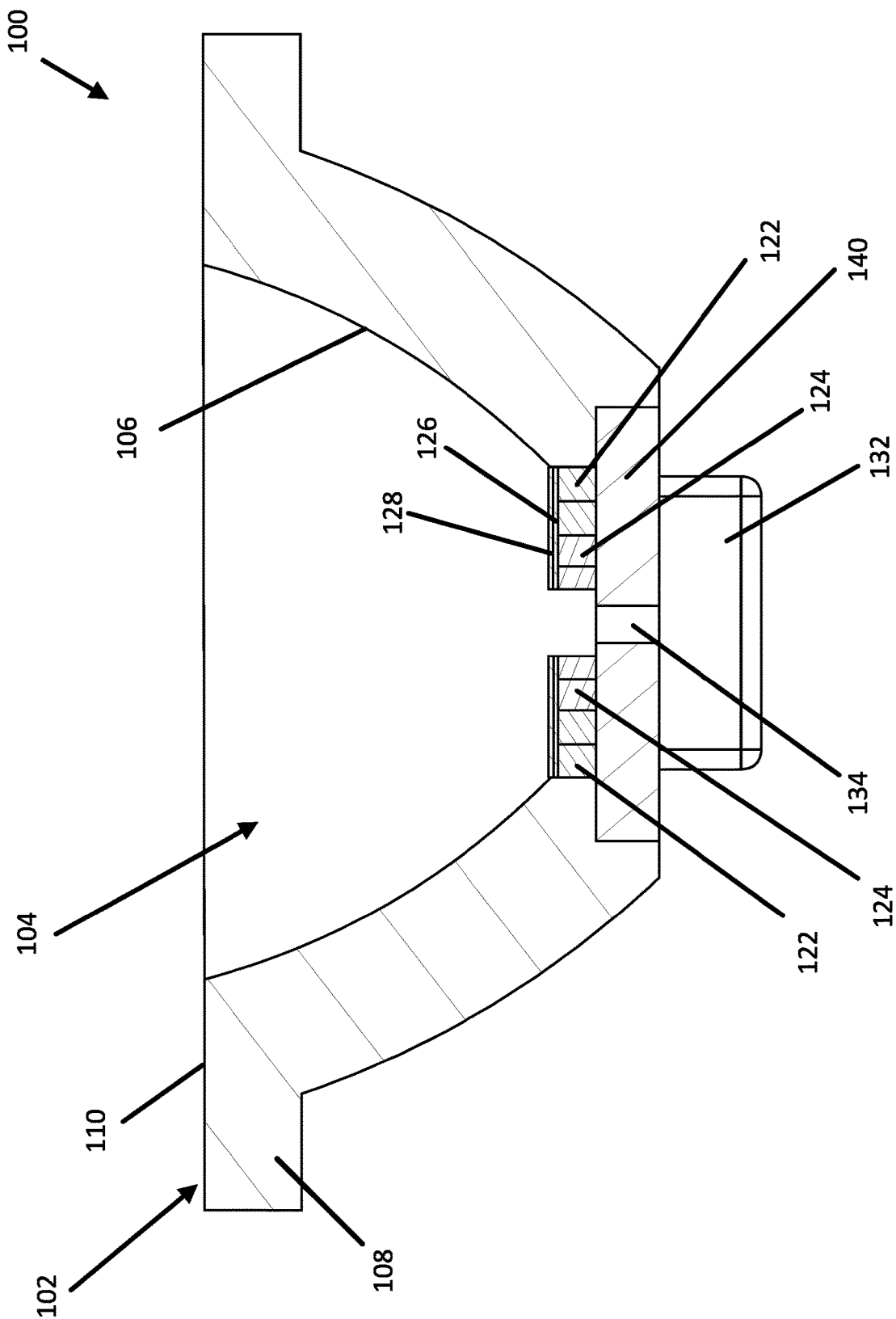
FIG. 4 is a cross-sectional view of the housing.

FIG. 3 illustrates a housing 102 of the wearable device 100. FIG. 4 is a cross-sectional view of the housing 102. Referring now to FIGS. 3 and 4, the housing 102 includes a rim 108 that defines an opening into an interior cavity 104. The rim 108 includes a surface 110 that is substantially planar. When the wearable device 100 is worn by the subject S, the surface 110 is in direct contact with a skin surface such as the chest wall so that the optical and acoustical signals from the optical unit 120 and acoustic unit 130, respectively, are able to penetrate the skin surface and reach the chest tissue of the subject S.

The interior cavity 104 is funnel shaped. In some examples, the interior cavity 104 has a concave profile that defines an apex at an end opposite the opening. In some examples, the concave profile is symmetrical about a central axis 114 (see FIG. 3). In some examples, the concave profile is parabolic such that the housing 102 is a parabolic reflector. In yet further examples, the interior cavity 104 is a compound parabolic concentrator (CPC), an off-axis reflector, or a freeform surface. In alternative examples, the interior cavity 104 can be asymmetrical with respect to the central axis 114.

In some examples, the opening of the interior cavity 104 can be about 1 inch to about ¾ of one inch in diameter. Additionally, while the rim 108 is shown as having a substantially circular shape, a plurality of shapes for the rim 108 are possible.

As shown in FIG. 4, the circuit board 140 is mounted inside the housing 102 toward an apex of the interior cavity 104. The light emitters 122, light sensors 124, and microphone 132 are each mounted to the circuit board 140 toward the apex of the interior cavity 104. The light emitters 122 and light sensors 124 are mounted to a first side of the circuit board 140 and face the opening of the interior cavity 104, and the first and second polarizers 126, 128 are mounted over the light emitters 122 and light sensors 124. As shown in FIG. 3, the first and second polarizers 126, 128 are mounted over the light emitters 122 and light sensors 124 such that the first and second polarizers 126, 128 are axially aligned about the central axis 114 of the interior cavity 104. The microphone 132 is mounted to an opposite, second side of the circuit board 140 that faces away from the opening of the interior cavity 104.

As shown in FIG. 3, the first and second polarizers 126, 128 each include an aperture 129 that allows the acoustic signals to pass through the first and second polarizers 126, 128. As shown in FIG. 4, the circuit board 140 also includes an aperture 134 that is axially aligned with the apertures 129 of the first and second polarizers 126, 128. The aperture 134 together with the apertures 129 on the first and second polarizers 126, 128 forms a passageway that allows the acoustic signals to enter the interior cavity 104 of the housing 102 and reach the microphone 132 positioned at the apex of the interior cavity 104. Advantageously, the passageway formed by the apertures 129, 134 improves the transmission of the acoustic signals to the microphone 132.

The concave surface profile of the interior cavity 104 funnels the acoustic signals from the opening of the interior cavity 104 to the microphone 132 located at the apex. The concave surface profile also funnels the reflected optical signals from the opening of the interior cavity 104 toward the light sensors 124 at the apex. Thus, the interior cavity 104 effectively collects and amplifies the acoustic and optical signals simultaneously.

To further enhance the funneling of the optical signals reflected toward the light sensors 124, the interior cavity 104 has a reflective interior surface 106 that is applied over the concave surface profile. The housing 102 is molded plastic while the reflective interior surface 106 is a coating applied to the molded plastic using one or more coating techniques during the manufacture of the wearable device 100. In some embodiments, the reflective interior surface 106 is electrodeposited nickel plating.

As described above, the wearable device 100 is preferably attached to the chest so that the microphone 132 is positioned next to the heart. Thus, unlike pulse oximeters that are clipped onto a fingertip to emit light signals that pass through the fingertip, the light emitters 122 and light sensors 124 are positioned on the same side of the subject's body (i.e., the chest), and the optical signals emitted from the light emitters 122 are reflected off the chest tissue and back to the light sensors 124. The chest tissue is a poor site for blood perfusion and the reflected optical signals are weaker than the signals typically recorded by pulse oximeters. To overcome these obstacles, the shape of the interior cavity 104 and the reflective interior surface 106 are used to amplify the optical signals that are reflected off the chest tissue for reading by the light sensors 124 which are positioned at the apex of the interior cavity 104. Also, the shape of the interior cavity 104 is used to reduce the potential for ambient light interference.

Additionally, the reflected optical signals include noise from the light that is reflected directly off the skin surface covering the chest tissue (i.e., glare). The glare from the skin surface is noise because it does not provide useful data on the oxygenated and deoxygenated hemoglobin which is used for the calculation of the $SpO_2$. Also, the glare from the skin surface does not provide useful data for detecting blood volume changes for the calculation of the pulse transit time (PTT) and blood pressure. To reduce this noise, the first and second polarizers 126, 128 filter the optical signals received by the light sensors 124 so that only optical signals that penetrates deeper into the chest tissue are received by the light sensors 124 for calculation of $SpO_2$ and blood pressure which results in a more accurate device.

Figure 5:
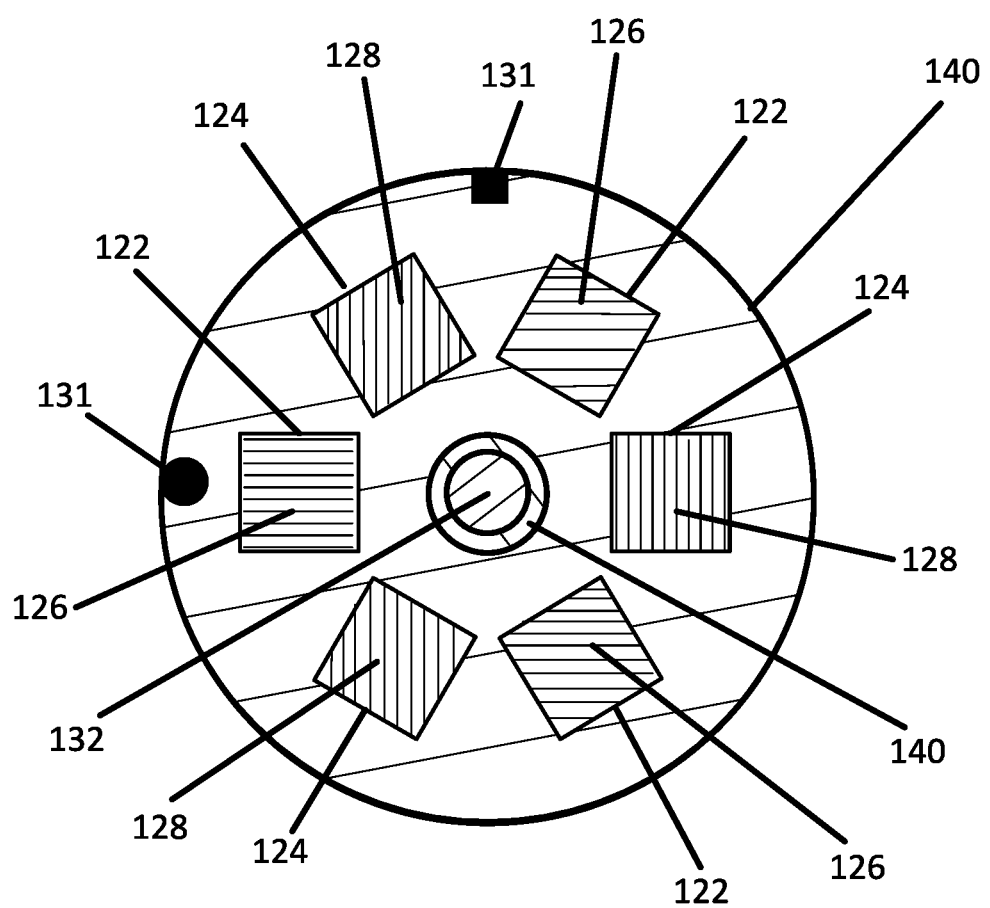
FIG. 5 illustrates an array of light emitters and light sensors.

FIG. 5 illustrates the light emitters 122 and light sensors 124 positioned around the circuit board 140, and with the first and second polarizers 126, 128 mounted over the light emitters 122 and the light sensors 124. Referring now to FIGS. 3-5, the first and second polarizers 126, 128 polarize the optical signals emitted from the light emitters 122 and filter the reflected optical signals received by the light sensors 124. As shown in FIG. 3, the first and second polarizers 126, 128 each include cutouts 127 that correspond to the shape, size, and location of the light emitters 122 and light sensors 124 on the circuit board 140.

In one embodiment, the first and second polarizers 126, 128 are linear polarizers that are both die cut from a single sheet of material that has a polarization running in one direction. In some examples, the sheet of material from which the first and second polarizers 126, 128 are die cut is plastic. In some further examples, the first and second polarizers 126, 128 are glass or crystal. In the embodiment illustrated in the figures, the first and second polarizers 126, 128 are circular-shaped discs mounted over the circuit board 140. In some examples, the circular-shaped discs each have an identical thickness of about 0.5 mm.

The first polarizer 126 is mounted over the light emitters 122 and light sensors 124 while the second polarizer 128 is mounted over the first polarizer 126. The first and second polarizers 126, 128 are shifted 90 degrees with respect to one another such that the optical signals emitted by the light emitters 122 and received by the light sensors 124 are 90 degrees out of phase due to the polarization of the first and second polarizers 126, 128.

The first and second polarizers 126, 128 each include one or more keys 131 to ensure that they are shifted 90 degrees with respect to one another when mounted over the light emitters 122 and light sensors 124. For example, the keys 131 can include one or more notches on the first and second polarizers 126, 128 that correspond to one or more features on the housing 102 or circuit board 140 to ensure the polarizers are shifted 90 degrees with respect to one another.

In one example, the cutouts 127 on the first polarizer 126 are positioned over the light sensors 124 such that the light emitters 122 are covered by the first polarizer 126 and the light sensors 124 are not covered by the first polarizer 126. The cutouts 127 on the second polarizer 128 are positioned over the light emitters 122 such that the light sensors 124 are covered by the second polarizer 128 and the light emitters 122 are not covered by the second polarizer 128.

In another example, the cutouts 127 on the first polarizer 126 are positioned over the light emitters 122 so that the light sensors 124 are covered by the first polarizer 126 and the light emitters 122 are not covered by the first polarizer 126. The cutouts 127 on the second polarizer 128 are positioned over the light sensors 124 such that the light emitters 122 are covered by the second polarizer 128 and the light sensors 124 are not covered by the second polarizer 128.

As shown in FIG. 5, lines running in a first direction (e.g., horizontal) represent a first polarity direction and are superimposed over the light emitters 122 by the first polarizer 126. Lines running in a second direction (e.g., vertical) represent a second polarity direction and are superimposed over the light sensors 124 by the second polarizer 128. Thus, the optical signals emitted from the light emitters 122 are polarized by the first polarizer 126 in the first polarity direction and the second polarizer 128 filters the reflected optical signals in the second polarity direction. As described above, the first and second polarizers 126, 128 are shifted 90 degrees such that the first and second polarity directions are orthogonal. Further, it is noted that FIG. 5 is provided as an illustrative example such that the first and second polarity directions of the first and second polarizers 126, 128, respectively, could be flipped with respect to one another.

As an alternative embodiment, instead of the disc shaped polarizers shown in FIGS. 3-5, the first and second polarizers 126, 128 can be pieces of polarized material individually mounted over each light emitter 122 and light sensor 124. For example, the first polarizers 126 can be individually mounted over each light emitter 122 to have a first polarity direction while the second polarizers 128 can be individually mounted over each light sensor 124 to have a second polarity direction. Additional alternative embodiments are contemplated.

The first and second polarizers 126, 128 operate to filter the reflected optical signals as follows. The optical signals reflected from the skin surface remain polarized in the first polarity direction. Since the second polarizer 128 is 90 degrees out of phase with respect to the first polarizer 126, the optical signals reflected from the skin surface are blocked from reaching the light sensors 124. In contrast, the optical signals that penetrate into the chest tissue are no longer polarized in the first polarity direction such that these optical signals are able to pass through the second polarizer 128 and reach the light sensors 124. Thus, the glare from the skin surface is blocked from reaching the light sensors 124, while the optical signals that penetrate the chest tissue are received by the light sensors 124. This reduces noise in the optical signals received by the light sensors 124, and can thus lead to more accurate measurements.

In alternative embodiments, the first and second polarizers 126, 128 are circular polarizers. In examples where the first and second polarizers 126, 128 are circular polarizers, the first polarizer is configured to polarize the optical signals emitted from the light emitters 122 in a clockwise or counter-clockwise direction. The second polarizer 128 is configured to have a circular polarity direction opposite that of the first polarizer 126 such that the second polarizer 128 blocks the optical signals reflected from the skin surface that remain polarized in the clockwise or counter-clockwise direction set by the first polarizer 126.

In alternative examples, the light emitters 122 emit polarized light. For example, the light emitters 122 can be lasers that emit polarized light. In certain examples, the polarized light emitted from light emitters 122 is linearly polarized light. In such examples, there is no need for a second polarizer such that the optical unit 120 uses only one polarizer. In such examples, the optical unit 120 has at least one polarizer 126, 128, and the polarized light emitted from the light emitters 122 that is reflected off a skin surface is filtered by the at least one polarizer 126, 128.

For example, the optical signals reflected from the skin surface remain polarized in the direction of the polarized light. In such examples, the at least one polarizer 126, 128 is orientated to block optical signals having a predetermined polarity direction such as the polarity direction of the polarized light from the light emitters 122. Thus, the optical signals reflected from the skin surface are blocked by the at least one polarizer 126, 128 from reaching the one or more light sensors 124, while the optical signals that penetrate into the chest tissue are no longer polarized in the direction of the polarized light such that these optical signals pass through the at least one polarizer 126, 128 and reach the one or more light sensors 124.

Figure 6:
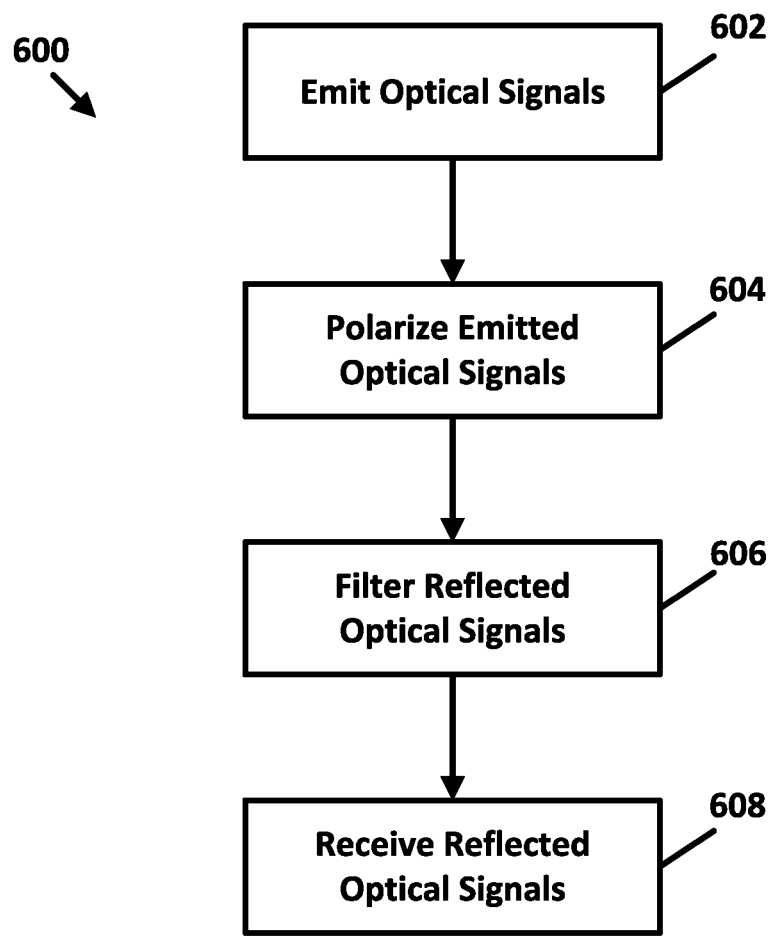
FIG. 6 illustrates a method for filtering reflected optical signals.

FIG. 6 illustrates a method 600 for obtaining vital signs that is performed by the wearable device 100. The method 600 includes an operation 602 of emitting optical signals using the light emitters 122. Next, the method 600 includes an operation 604 of polarizing the emitted optical signals in a first direction by using the first polarizer 126. Method 600 includes an operation 606 of filtering the reflected optical signals by using the second polarizer 128 to block the reflected optical signals that do not penetrate into a tissue. Next, method 600 includes an operation 608 of using the light sensors 124 to receive reflected optical signals that penetrate into the tissue. In some examples, the tissue is a chest tissue located next to the heart of the subject S.

The method can further include using the reflected optical signals that penetrate into the tissue to measure a vital sign. For example, the reflected optical signals can be used to calculate peripheral oxygen saturation. Alternatively, or in addition to calculating the peripheral oxygen saturation, the reflected optical signals can be used to calculate blood pressure.

Figure 7:
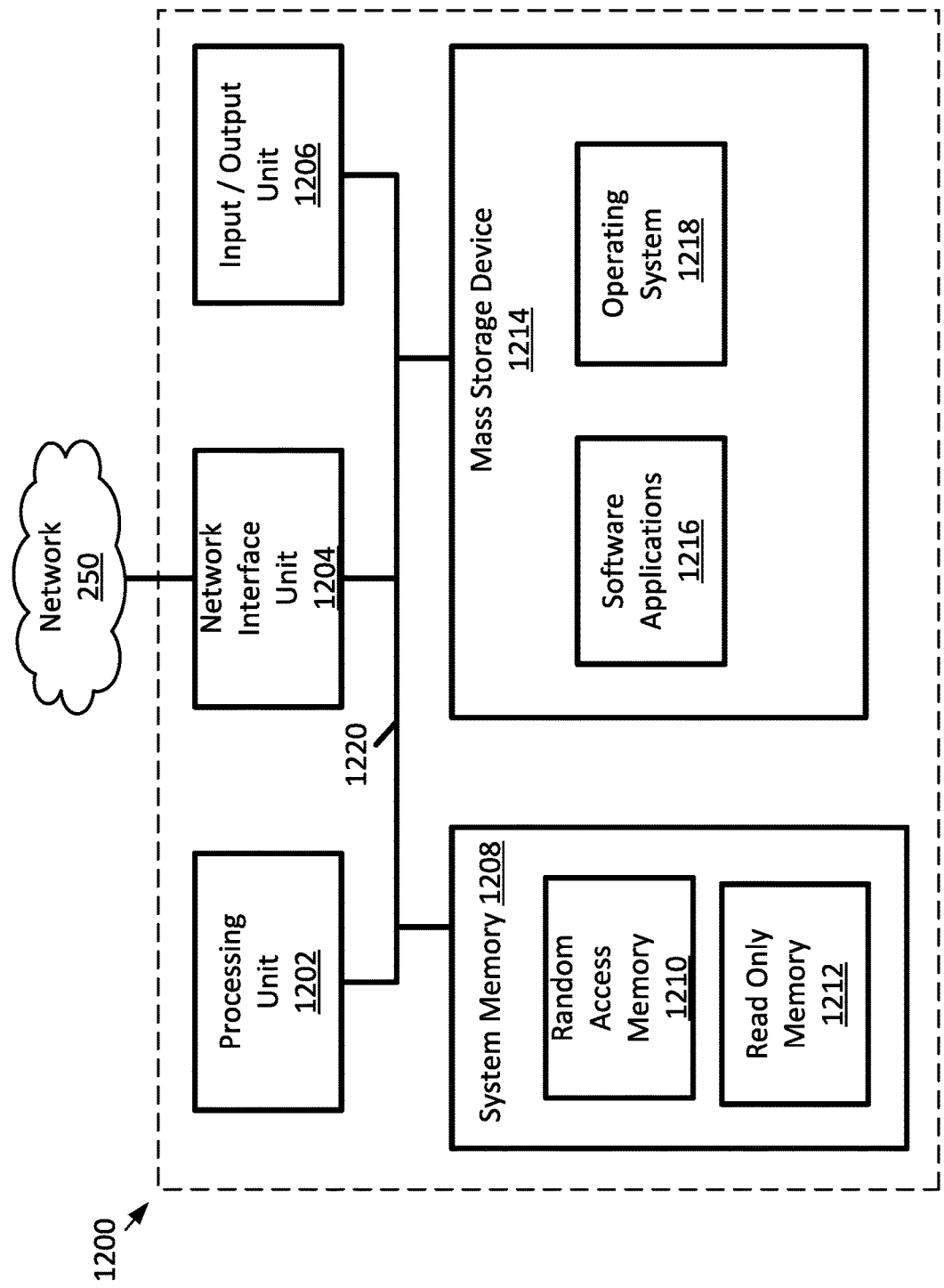
FIG. 7 illustrates an exemplary architecture of a computing device that can be used to implement aspects of the present disclosure.

FIG. 7 illustrates an exemplary architecture of a computing device 1200 which can be used to implement aspects of the present disclosure such as the functions of the wearable device 100 and monitor device 200 described above. The computing device 1200 includes a processing unit 1202, a system memory 1208, and a system bus 1220 that couples the system memory 1208 to the processing unit 1202. The processing unit 1202 is an example of a processing device such as a central processing unit (CPU). The system memory 1208 includes a random access memory ("RAM") 1210 and a read-only memory ("ROM") 1212. A basic input/output logic containing the basic routines that help to transfer information between elements within the computing device 1200, such as during startup, is stored in the ROM 1212.

The computing device 1200 can also include a mass storage device 1214 that is able to store software instructions and data. The mass storage device 1214 is connected to the processing unit 1202 through a mass storage controller (not shown) connected to the system bus 1220. The mass storage device 1214 and its associated computer-readable data storage media provide non-volatile, non-transitory storage for the computing device 1200.

Although the description of computer-readable data storage media contained herein refers to a mass storage device, it should be appreciated by those skilled in the art that computer-readable data storage media can be any available non-transitory, physical device or article of manufacture from which the device can read data and/or instructions. The mass storage device 1214 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, or any other medium which can be used to store information and which can be accessed by the device.

The computing device 1200 may operate in a networked environment using logical connections to remote network devices through the network 250, such as a local network, the Internet, or another type of network. The device connects to the network 250 through a network interface unit 1204 connected to the system bus 1220. The network interface unit 1204 may also be utilized to connect to other types of networks and remote computing systems.

The computing device 1200 can also include an input/output controller 1206 for receiving and processing input from a number of input devices. Similarly, the input/output controller 1206 may provide output to a number of output devices.

The mass storage device 1214 and the RAM 1210 can store software instructions and data. The software instructions can include an operating system 1218 suitable for controlling the operation of the device. The mass storage device 1214 and/or the RAM 1210 also store software instructions 1216, that when executed by the processing unit 1202, cause the device to provide the functionality of the device discussed in this document. For example, the mass storage device 1214 and/or the RAM 1210 can store software instructions that, when executed by the processing unit 1202, cause the wearable device to send or receive vital signs measurements.

The various embodiments described above are provided by way of illustration only and should not be construed to be limiting in any way. Various modifications can be made to the embodiments described above without departing from the true spirit and scope of the disclosure.

What is claimed is:

1. A wearable device for sensing vital signs comprising:
    a housing defining an interior cavity;
    an optical unit positioned inside the interior cavity, the optical unit having:
        one or more light emitters that emit optical signals;
        at least one polarizer orientated to block optical signals having a predetermined polarity direction; and
        one or more light sensors that receive optical signals that pass through the at least one polarizer;
        wherein the at least one polarizer includes first and second polarizers each mounted over the one or more light emitters and the one or more light sensors, the first polarizer being orientated to polarize the optical signals emitted from the one or more light emitters in a first polarity direction, and the second polarizer being orientated with respect to the first polarizer such that the second polarizer blocks optical signals that are reflected back in the first polarity direction, and the one or more light sensors receive optical signals that pass through the second polarizer; and
    an acoustic unit positioned inside the interior cavity, the acoustic unit having:
        a microphone to receive acoustic signals that enter into the interior cavity, the acoustic signals being used to non-invasively estimate blood pressure.

2. The device of claim 1, wherein the one or more light emitters emit polarized optical signals.

3. The device of claim 1, wherein the interior cavity has a concave profile that defines an apex opposite an opening, and the optical unit and acoustic unit are mounted at the apex.

4. The device of claim 1, wherein the interior cavity has a reflective interior surface.

5. The device of claim 1, wherein the first and second polarizers are axially aligned about a central axis of the interior cavity.

6. The device of claim 5, wherein the second polarizer is shifted 90 degrees with respect to the first polarizer.

7. The device of claim 6, wherein the first and second polarizers each includes an aperture allowing the acoustic signals to pass through the first and second polarizers.

8. The device of claim 7, further comprising a circuit board having an aperture forming a passageway with the apertures of the first and second polarizers, the passageway allowing the acoustic signals to reach the microphone which is positioned on an opposite side of the circuit board as the one or more light emitters and the one or more light sensors.

9. The device of claim 1, wherein the first and second polarizers are each circular discs having one or more cutouts corresponding to locations of the one or more light emitters and the one or more light sensors, respectively.

10. The device of claim 9, wherein the one or more cutouts of the first polarizer are positioned over the one or more light sensors, the one or more light emitters are covered by the first polarizer, and the one or more the light sensors are not covered by the first polarizer.

11. The device of claim 10, wherein the one or more cutouts of the second polarizer are positioned over the one or more light emitters, the one or more light sensors are covered by the second polarizer, and the one or more light emitters are not covered by the second polarizer.

12. The device of claim 1, wherein the optical signals received by the one or more light sensors are used to non-invasively measure peripheral oxygen saturation.

13. The device of claim 12, wherein the wearable device non-invasively measures the blood pressure and peripheral oxygen saturation simultaneously.

14. A wearable device for sensing vital signs comprising:
    a housing defining an interior cavity;
    an optical unit positioned inside the interior cavity, the optical unit having:
        one or more light emitters that emit optical signals;
        a first polarizer orientated to polarize the optical signals emitted from the one or more light emitters in a first polarity direction;
        a second polarizer orientated with respect to the first polarizer to block optical signals reflected back in the first polarity direction; and
        one or more light sensors that receive reflected optical signals that pass through the second polarizer, the reflected optical signals being used to non-invasively measure peripheral oxygen saturation;

wherein the first and second polarizers are each mounted over the one or more light emitters and the one or more light sensors.

15. The wearable device of claim 14, further comprising an acoustic unit positioned inside the interior cavity, the acoustic unit having a microphone to receive acoustic signals that enter into the interior cavity, the acoustic signals being used to non-invasively estimate blood pressure.

* * * * *